US009220875B2

(12) United States Patent
Scheller et al.

(10) Patent No.: US 9,220,875 B2
(45) Date of Patent: *Dec. 29, 2015

(54) PHARMACEUTICAL-COATED MEDICAL PRODUCTS, THE PRODUCTION THEREOF AND THE USE THEREOF (71) Applicant: Invatec Technology Center Gmbh, Frauenfeld (CH)

(72) Inventors: Bruno Scheller, Saarbrucken (DE); Ulrich Speck, Berlin (DE)

(73) Assignee: Invatec Technology Center GmbH, Frauenfelf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/086,813

(22) Filed: Nov. 21, 2013

(65) Prior Publication Data
US 2014/0155825 A1 Jun. 5, 2014

Related U.S. Application Data (63) Continuation of application No. 12/671,910, filed as application No. PCT/DE2008/001285 on Aug. 1, 2008, now Pat. No. 8,608,689.

(30) Foreign Application Priority Data

Aug. 3, 2007 (DE) .......................... 10 2007 036 685

(51) Int. Cl.
*A61M 25/12* (2006.01)
*A61F 2/958* (2013.01)
(Continued)

(52) U.S. Cl.
CPC .............. *A61M 25/10* (2013.01); *A61L 29/145* (2013.01); *A61L 29/16* (2013.01); *A61L 2300/204* (2013.01); *A61L 2300/21* (2013.01); *A61L 2300/22* (2013.01); *A61L 2300/602* (2013.01);
(Continued)

(58) Field of Classification Search
CPC .............. A61M 2025/1031; A61M 2025/105; A61M 2025/1075; A61M 2025/1004; A61M 2025/1086; A61M 2025/1088; A61M 25/10
See application file for complete search history.

(56) References Cited

U.S. PATENT DOCUMENTS 5,102,402 A  4/1992  Dror et al.
5,304,121 A  4/1994  Sahatjian
(Continued)

FOREIGN PATENT DOCUMENTS

DE  102004046244  3/2006
DE  102004048265  4/2006
(Continued)

OTHER PUBLICATIONS

PCT International Preliminary Report on Patentability for PCT/DE2008/001456 filed on Aug. 7, 2008 in the name of Bruno Scheller, et al.
(Continued)

*Primary Examiner* — Bhisma Mehta
*Assistant Examiner* — William Frehe (57) ABSTRACT This present invention concerns a new combination of balloon catheters and formulations containing active substances that adhere to the surface of the balloon membrane. Furthermore the present invention concerns coating processes for the manufacture of these balloon catheters as well as their use in the treatment and prophylaxis of vascular diseases.

32 Claims, 3 Drawing Sheets (51) Int. Cl.
*A61M 25/10* (2013.01)
*A61L 29/14* (2006.01)
*A61L 29/16* (2006.01)
*A61M 25/00* (2006.01)

(52) U.S. Cl.
CPC .... *A61M 25/0045* (2013.01); *A61M 2025/0057* (2013.01); *A61M 2025/105* (2013.01); *A61M 2025/1031* (2013.01)

(56) References Cited

U.S. PATENT DOCUMENTS

| | | | |
|---|---|---|---|
| 5,370,614 | A | 12/1994 | Amundson |
| 5,893,840 | A | 4/1999 | Hull et al. |
| 6,306,166 | B1 | 10/2001 | Barry |
| 7,105,018 | B1 | 9/2006 | Yip |
| 8,608,689 | B2 * | 12/2013 | Scheller et al. ......... 604/103.02 |
| 2002/0165521 | A1 | 11/2002 | Cioanta et al. |
| 2003/0064965 | A1 | 4/2003 | Richter |
| 2003/0181973 | A1 | 9/2003 | Shaota |
| 2004/0224003 | A1 | 11/2004 | Schultz |
| 2005/0003417 | A1 | 1/2005 | Mace et al. |
| 2005/0059965 | A1 | 3/2005 | Eberl et al. |
| 2006/0002973 | A1 | 1/2006 | Barry |
| 2006/0020331 | A1 * | 1/2006 | Bates et al. ................. 623/1.49 |
| 2006/0034894 | A1 | 2/2006 | Lakkis |
| 2007/0003596 | A1 | 1/2007 | Tittelbach et al. |
| 2007/0060883 | A1 | 3/2007 | Doty |
| 2007/0287956 | A1 | 12/2007 | Tal |
| 2008/0015500 | A1 | 1/2008 | Herweck et al. |
| 2008/0021385 | A1 | 1/2008 | Barry et al. |
| 2008/0114331 | A1 | 5/2008 | Holman et al. |
| 2008/0118544 | A1 | 5/2008 | Wang |
| 2009/0270801 | A1 | 10/2009 | Shimada et al. |
| 2009/0270802 | A1 | 10/2009 | Nishide et al. |
| 2010/0209472 | A1 | 8/2010 | Wang |
| 2011/0099789 | A1 | 5/2011 | Ewing et al. |

FOREIGN PATENT DOCUMENTS

| | | |
|---|---|---|
| EP | 0519063 | 12/1992 |
| EP | 1372737 | 8/2006 |
| WO | WO92/11890 | 7/1992 |
| WO | WO95/03083 | 2/1995 |
| WO | WO9511055 | 4/1995 |
| WO | WO9639940 | 12/1996 |
| WO | WO00/21584 | 4/2000 |
| WO | WO01/49268 | 7/2001 |
| WO | WO0152772 | 7/2001 |
| WO | WO02/076509 | 10/2002 |
| WO | WO03039612 | 5/2003 |
| WO | WO03/099346 | 12/2003 |
| WO | WO2004/006976 | 1/2004 |
| WO | WO2004/022124 | 3/2004 |
| WO | WO2004/028582 | 4/2004 |
| WO | WO2004/028610 | 4/2004 |
| WO | WO2005089855 | 9/2005 |
| WO | WO9639949 | 12/2006 |
| WO | WO2007/008829 | 1/2007 |
| WO | WO2007/090385 | 8/2007 |
| WO | WO2008/063576 | 5/2008 |
| WO | WO 2014/025526 A1 | 2/2014 |

OTHER PUBLICATIONS

PCT International Search Report for PCT/DE2008/001456 filed on Aug. 7, 2008 in the name of Bruno Scheller et al.
PCT Written Opinion for PCT/DE2008/001456 filed on Aug. 7, 2008 in the name of Bruno Schelller et al.
Hayakawa E., et al. Viscosity Study on Self-Association of Doxorubicin in Aqueous Solution, Chemical Pharm. Bulletin 1991; 39:1281-1286.
Kutryk M. et al., Local Intracoronary Administration of Antisense Oligonucleotide Against C-MYC for the Prevention of In-stent Restenosis: Results of the Randomized Investigation by the Thoraxcenter of Antisense DNA Using Local Delivery and IVUS After Coronary Stenting Trial, J. Am. Coll. Cardiol. 2002; 39:281-287.
Kiesz R. et al., Local Delivery of Enoxaparin to Decrease Restonsis After Stenting: Results of Initial Multicenter Trial: Polis-American Local Lovenox NIR Assessment Study, Circulation 2001; 103:26-31.
Muni N. et al., Coronary Drug-elating Stent Development: Issues in Trial Design, Am Heart J 2005; 149:415-433.
Scheller B. et al., Prevention of Restenosis: Is Angioplasty the Answer?, Heart 2007; 95:539-541.
Scheller B et al., Treatment of Coronary In-Stent Restenosis With a Paclitaxel-Coated Balloon Catheter, N Engl J Med 2006; 355: 2113-2124.
Schillinger M. et al. Balloon Angioplasty versus Implantation of Nitinol Stents in the Superficial Femoral Artery, N Engl J Med 2006; 354: 1879-1888.
Scheller B et al. Paclitaxel Balloon Coating, a Novel Method for Prevention and Therapy of Restenosis, Circulation 2004; 110:810-814.
Tepe G et al. Local Delivery of Paclitaxel to Inhibit Restenosis during Angioplasty of the Leg N Engl J 2008: 258; 689-699.
Levin A. et al., Specific Binding to Intracellular Proteins Determines Arterial Transport Properties for Rapamycin and Paclitaxel PNAS 2004; 101: 9463-9467.
Yang W. et al., Arsenic Trioxide Eluting Stent Reduces neointimal Formation in a Rabbit Iliac Artery Injury Model Cardio Res 2006; 72; 483-493.
Cremers, B. et al., V1742-Paclitaxel-beschichtete PTCA-Katheter: Gibt es Unterschiede? Einfluss von PACCOCATH® and DIOR® Ballon kathetern auf die Neointimaproliferation an Schweinekoronarien, Clinical Research in Cardiology 2008, 97-Suppl 1.
PCT International Search Report for PCT.DE2008/001285 filed on Jan. 8, 2008 in the name of INNORA Gmbh.
PCT Written Opinion for PCT/DE2008/001285 filed on Jan. 8, 2008 in the name of INNORA Gmbh.

* cited by examiner

PHARMACEUTICAL-COATED MEDICAL PRODUCTS, THE PRODUCTION THEREOF AND THE USE THEREOF

RELATED APPLICATIONS

This application is a Continuation of and claims the benefit of U.S. patent application Ser. No. 12/671,910 filed Mar. 2, 2010, which is the US national stage of International Application PCT/DE2008/001285 filed on Aug. 1, 2008 which, claims priority to German Application 102007036685.1 filed Aug. 3, 2007. The disclosures of which are herein incorporated by reference in their entirety.

MEDICAL AND TECHNICAL BACKGROUND

Many diseases do not affect the whole organism at the same time, but are restricted to particular kinds of tissue and are frequently restricted to certain limited areas of tissue or to certain parts of organs. Examples can be found in tumorous diseases, joint diseases and vascular diseases, and in particular with solid tumours and arterial vascular diseases. Pharmacotherapy of these diseases generally takes place by the oral or intravenous administration of pharmaceutical substances which distribute themselves throughout the whole body and in many cases can cause undesirable effects in healthy tissue and in healthy organs, particularly with severe illnesses. These undesirable effects can limit the therapeutic applications. Selective treatment of the diseased tissue is achieved by means of specific pharmaceutical substances which bind to the diseased tissue (e.g. antibodies) during the chosen method of application or by selective administration e.g. by direct application to the diseased tissue, or by being supplied by a catheter in the blood vessel that is affected. In cases of selective administration there are problems which arise because of the mainly short duration of the effects of the pharmaceutical substances and because of the invasive methods of application, since any repeated administration is out of the question.

Problems for pharmacotherapy are caused by the special method of application and the necessity of achieving a significant prophylactic or therapeutic effect in one single application. In the past 10 years significant success has been achieved particularly in the treatment of arteriosclerotic vascular changes. Such changes frequently occur in localised areas. They lead to constrictions or occlusions of specific sections of the blood vessels which impair or prevent the supply of blood to the tissue which lies on the other side of the blockage. This mainly affects the heart, the legs, the brain, the kidneys and surgically altered vessels such as dialysis shunts. Narrowing of these vessels can be treated with a catheter which is introduced percutaneously and which can be introduced into the relevant blood vessels without causing a large amount of injury because of its small diameter. They mostly contain a balloon in the distal part which is folded around the catheter shaft and which can be expanded by means of a fluid. When it is still folded this balloon is pushed into the restricted part of the blood vessel where it is expanded for a short time (ranging from a few seconds to a few minutes) so that the original vessel lumen is restored and the blood can again pass through the originally constricted area.

At the same time a tubular piece of metal mesh (vessel support, stent) can be introduced to support the opened vessel lumen. This can be either mounted on the folded balloon or it can be released as an elastic, self-expanding stent by means of a special catheter.

While the initial success rate is over 90%—measured by the widening of the vessel lumen to approaching the size before the constriction appeared—with many patients a renewed constriction can occur several months after treatment (restenosis). The most significant cause is from the excessive proliferation of cells in the vascular wall triggered by injuries caused during the violent expansion of the vessel. This affects the smooth muscle cells in particular, which do not come to a standstill after the healing of the original injury. This process could be almost completely suppressed in the coronary arteries by coating the stent with antiproliferative pharmaceutical products. A requirement is that the pharmaceutical product is released slowly (i.e. over days and weeks) from a polymer matrix. The disadvantage of coating the stent is that healing is inhibited from taking place. Thrombi can form on the struts of the stent as long as they are in direct contact with the blood. Thrombi can lead to a sudden and total vascular occlusion, to infarction and to death. The struts must therefore become rapidly and permanently overgrown by an endothelial layer. This is inhibited by the sustained release of an active substance that inhibits cell proliferation.

There are no controlled studies available for peripheral arteries which demonstrate effective prophylaxis of restenosis by coating stents with pharmaceutical products. Certain self-expanding nitinol stents do however appear to reduce the restenosis rate to some extent without a coating of a pharmaceutical product being necessary (Schillinger M, Sabeti S, Loewe C et al. Balloon angioplasty versus implantation of nitinol stents in the superficial femoral artery N Engl J Med 2006; 354: 1879-88).

The coating of balloons is described in principle in EP 1 372 737 A. The active substance is applied by, for example, immersing the balloon in a solution of the active substance. In WO 2004/028582 A the possibilities of coating balloons in various stages of folding are described including when the balloons are preformed.

Constricted arteries, often connected with solid calcification, can mainly be expanded to their original lumen only by using a high pressure (8 to 20 atmospheres). This is achieved by using pressure resistant balloons whose diameter does not significantly change with increasing internal pressure.

The balloon forms a rigid cylinder which lies against the vascular wall as long as the diameter of the vascular lumen before the expansion of the balloon is smaller than the diameter of the balloon. With a suitably high pressure an active substance applied to the outside of the balloon is pressed against the expanded vascular wall.

Localised treatment using pharmaceutical substances may also be necessary without stretching the vascular lumen. Examples are the treatment of arteries following the removal of plaque material with mechanical (e.g. atherectomy catheters), thermal processes (e.g. lasers) or the treatment of changes to the vascular wall which do not lead to flow inhibiting stenoses (e.g. vulnerable plaques, overlying thrombi). Any overstretching and damage to the vessel is undesirable in such cases. If the customary angioplasty balloons are selected with a diameter which does not lead to any stretching of the vessel then their membrane only comes into contact with the irregularly shaped vascular wall in a few places and only transfers the pharmaceutical substance in those places.

STATE OF THE ART

In WO 02/076509 A it was first disclosed that exposure of the damaged vascular wall lasting a few seconds was sufficient to inhibit a restenosis from developing over a period of several weeks. The same was described with a balloon catheter coated with a pharmaceutical product which on contact with the vascular wall released the active substance in an immediately bioavailable form.

In several earlier and later patent applications the coating of balloon catheters with pharmaceutical products is described where continual attempts were indeed made to achieve sustained levels of the active substances despite the short time the angioplasty balloon was in contact with the vascular wall. The methods of coating that were generally described produced products that demonstrated a significant lack of quality and/or which were expensive and time-consuming to manufacture.

Lipophilic, active substances which were slightly soluble in water were preferred over hydrophilic active substances, because lipophilic substances are easy to apply using highly volatile organic solvents. It is not so easy for them to be prematurely washed away from the surface of the balloon during the handling of the devices and when they are in the bloodstream. They are also more rapidly absorbed by the cells and remain there for longer. In individual cases hydrophilic active substances such as methotrexate or arsenic trioxide have been used on stents to inhibit restenosis by neointimal hyperplasia (US 20060348947; Yang W, Ge J, Liu H et al. Cardiovascular Research 2006; 72:483-493). The active substances are embedded in water insoluble polymers from which they are only released slowly. In this way premature loss of the active substance is inhibited. The same is true for the use of hydrophilic cytostatics for the antimicrobial coating of indwelling catheters and other implants (WO003099346).

In fact only the catheter coatings disclosed in WO 02/076509 A and WO 2004/028582 A led to effective products which reduce the extent and frequency of restenosis following vascular dilatation (Scheller B, Hehrlein C, Bocksch W, Rutsch W, Haghi D, Dietz U, Böhm M, Speck U. Treatment of Coronary In-stent Restenosis with a Paclitaxel-coated Balloon Catheter. N Engl J Med 2006; 255: 2113-2124, Tepe G, Zeller T, Albrecht T, Heller S, Schwarzwälder U, Beregi J-P, Claussen C D, Oldenburg A, Scheller B, Speck U. Local delivery of paclitaxel to inhibit restenosis during angioplasty of the leg. N Engl J Med 2008; 358:689-699).

In documents concerning the state of the art technology many active substances and matrix substances are named with which coating can be carried out. Preferred among the substances mentioned are those which inhibit cell proliferation and those which have anti-inflammatory or anticoagulant properties.

The additives mentioned were contrast media, matrix or gel-forming additives e.g. lipids or polymers which are usually used in pharmacy, heparin, castor oil (WO 02/076509) or matrix substances up to 5000 Da, hydrophilic dyes such as, indocyanine green, fluorescein, methylene blue, sugar, sugar derivates, low molecular weight PEG, organic and inorganic salts, benzoates, salicylates (WO 2004/028582) polymers, also for coating of pharmaceutical products (EP 0519063; U.S. Pat. No. 5,102,402), polymers such as starch, gelatine, PEG, albumin, chitosan, β-cyclodextrins, hydroxyethyl cellulose as well as lipids, amphiphilic phospholipids and radio-contrast media including amphiphilic iodoxamic acid (DE 102004046244), substances which increase cell permeability such as linoleic acid, linolenic acid, oleic acid, stearic acid, phenyl salicylate, antioxidants such as vitamin E, tocotrienols, tocopherols, as well as nitrophenyl octyl ether, bis (ethylhexyl)sebacate, diisododecyl phthalate, N-methylpyrrolidone, butylhydroxyanisol, butylhydroxtoluene, phosphorylcholine and polymers (WO 2004/022124); oils, fatty acids, fatty acid esters, contrast medium derivatives, amino acids, peptides, vitamins, o-phosphoserine, neutral or charged amphiphilic substances, salts (WO 2007090385); amphiphilic substances such as polyethylene glycol ester, fatty acid esters of sugars, polyglyceryl-6-fatty acid ester, polyglyceryl-10-fatty acid ester, sucrose monopalmitate, surfactants with lipid chains which incorporate themselves in lipid membranes, ionic and non-ionic detergents, substances with more than 4 hydroxyl, carboxyl or amino groups, sorbitan fatty acid ester, substances with a phenol ring, sodium cholate, sodium taurocholate; furthermore there are vitamins and derivatives, polyethylene glycol as an additive to a suspension of pharmaceutical particles: organic acids, salts, anhydrides, amino acids and peptides including fibrinogen, many functionally defined substances and coatings (US 2008/0118544). Only a few of these additives are really useful and often this is only for certain active substances and coatings. Many of the additives mentioned have effects which damage the cell membrane (detergents, amphiphilic substances), inhibit the rapid absorption of the active substances into the cells or they are themselves unstable. For the expert it is mainly unpredictable which additive is to be used with which active substance and in what dosage.

Possibilities to prolong the release of the active substances are described in detail. Methods of coating the balloons have however previously received little attention, although this is exceedingly important in order to satisfy the requirements for a product that can be reproducibly manufactured and in order for the product to deposit an effective dose in the targeted tissue within a period ranging from a few seconds up to a maximum time of several minutes.

The following processes have previously been described for the coating of the balloons:

WO 92/11890 A describes the use of microcapsules as carriers of the pharmaceutical product: the microcapsules ensure the prolonged release of the active substances. The microcapsules are held in place by means of a binding agent or by fusion to the surface of the balloon or the recesses in the balloon membrane. Application takes place by immersion or by spraying. Apart from a description of the recesses in the balloon membrane there are no indications of how a particular active substance could be applied to the balloon in such a way that that it adheres sufficiently securely on the journey through the insertion sheath and through fast following blood and for it to subsequently be completely released when the balloon is expanded.

According to WO 2004/006976 A active substances are applied onto a rough or textured balloon surface by immersion, by absorption or by spraying where the balloon is in the expanded state. A hydrophilic layer between the balloon membrane and the lipophilic pharmaceutical product should facilitate the detachment of the active substance.

In WO 00/21584 A pharmaceutical products that are insoluble in water are described as being applied to a balloon by immersion, by spraying or by being applied drop wise by means of a pipette. The balloon is coated with a polymer which absorbs the active substance. The release was incomplete during the periods of observation which lasted from minutes to hours.

The preferred placement of the coating under the longitudinal folds of the balloon catheter is described in detail in WO 2007090385 where several examples are provided. The mixtures containing the active substances are applied beneath the folds by means of processes involving the use of pipettes, spraying or injection. While a precise method of coating is claimed the examples document that there was widespread variation in the doses.

US 2003/064965 A claims a rapid release of pharmaceutical preparations from balloon catheters where the preparations themselves should ensure that there is a controlled (i.e. prolonged) release. For this purpose the active substances are used in the form of capsules e.g. as liposomes, colloids, microparticles, aggregates or flocculated suspensions. Substances proposed for use as matrices are fibrin gels, hydrogels and also glucose. A porous layer should protect the coating.

A protective tube over the coating is also described in US 2006/002973 A. The preparations are applied by spraying, immersion, rolling, brushing and by binding to the balloon membranes by the action of solvents or the use of adhesives.

Furthermore the following are disclosed as coating processes: spraying in a vacuum, also using suspensions or emulsions (DE 10 2004 048 265 A), the use of fats and oils (US 2004/224003 A, WO 2003/039612 A), the use of substances or conditions which cause the release of the pharmaceutical product (WO 96/39949 A), the use of lipophilic hydration inhibitors (WO 2005/089855 A), coating the balloon with preassembled stents (e.g. DE 10 2004 046 244 A; US 2005/0033417 A) and the protection of the coated balloon by means of coverings which are only retracted shortly before the balloon is expanded.

In EP 1 372 737 A and WO 2004/028582 A processes are disclosed which describe amongst other things coating balloon catheters with lipophilic active substances which immediately become bioavailable when the balloons are expanded. The coating takes place by immersion, by brushing, spraying or by using a device for measuring volume.

The importance of the uniformity of the surface coating is taken into account in WO 2004/006976 A by coating the balloon in its expanded state with all parts of its surface equally accessible from outside. In WO 2001/052772 A this problem is addressed for various kinds of product by the use of a vibrator during the coating process.

With the exception of the coated balloons described in EP 1 372 737 A and WO 2004/028582 A none of the previously described balloon catheters proves itself to be effective from a consideration of the improvements in clinical success achieved, or in terms of the desired biological and therapeutic targets being achieved from animal experiments alone. The methods of coating are only described vaguely or the described methods lead to products with considerable shortcomings.

In spite of the very high levels of efficacy the balloon catheters described in patent specifications EP 1 372 737 A and WO 2004/028582 demonstrate disadvantages which are undesirable in a pharmaceutical product. Many of the active substances detailed in all the previously mentioned patent specifications either do not produce any yield at the site of pharmacological action, or produce a completely inadequate yield using catheters that are coated according to the methods described, or there are no methods described by which an expert can arrive at a usable product that corresponds to state of the art technology. The previously described coatings of pharmaceutical substances for balloon catheters are either insufficiently effective or insufficiently reliably effective, and amongst other things because the pharmaceutical substances are too unevenly distributed, because they adhere too strongly or do not adhere strongly enough to the balloon membrane, because they dissolve too quickly or too slowly, or because they contain additives which for their part can damage the vascular wall, or because they are too unnecessarily complex in their construction leading to disadvantages in terms of their manufacture, reproducibility, stability and application.

Balloon catheters for the transfer of active substances to the vascular wall have not previously been described which do not at the same time cause any overstretching and damage to the vascular wall. If the customary angioplasty balloons are selected with a diameter which does not produce any stretching of the vessel then their membrane only comes into contact with the irregularly shaped vascular wall in a few places and only transfers the pharmaceutical substance in those places.

Definitions

Medicinal product: Instruments for the treatment or prophylaxis of diseases, and if necessary supported by the use of pharmacologically effective substances;

Balloon catheter: A catheter with an expandable distal segment;

Balloon membrane: A membrane or a balloon membrane characterised by an outer covering fitted to the catheter balloon which comes into contact with the vascular wall; preferred membranes are smooth membranes and membranes which are coated in the folded state; the balloon catheters which are usually used demonstrate smooth balloon membranes. The texturising or roughening of the balloon membranes requires special procedures to be adopted during manufacture;

Stent: A tubular structure to be placed in cavities or tissues (vessel supports);

Active substance: A biological or medically effective substance; pharmaceutical substances are preferred i.e. permitted active substances that contain pharmaceuticals;

Additive: A substance without any intended biological effect;

Matrix substance: A substance which surrounds an active substance or holds it firmly in some other way; the matrix itself may display a biological effect;

Lipophilic Substance: Affinity to fats; measured as a distribution coefficient between a solvent that dissolves fats and an aqueous solvent;

Hydrophilic Substance: Affinity to water; measured as a distribution coefficient between a solvent that dissolves fats and an aqueous solvent;

Water soluble and/or hydrophilic substances: Biologically effective substances which either as they are, or in the form of a salt dissolve at a rate of at least 1 mg/ml (preferably at 5 mg/ml, and more preferably at 20 mg/ml) in water or an aqueous medium such as plasma or blood or which demonstrate a distribution coefficient butanol/water of less than 0.5;

Sparingly soluble: By the term 'sparingly soluble' means that the solubility in water of the substance concerned is less than 5 mg/ml and preferably less than 1 mg/ml;

Hydrophilic solvents: Solvents in which at room temperature at least 1% by volume of water dissolves and preferably 10% by volume of water;

Immediate bioavailability: Transfer of the active substance to the tissue during the short period of balloon dilatation without the dissolution of the active substance or its release into the tissue being delayed by any special treatments like encapsulation;

Immediate release: Means that when the balloon is expanded the effective dose of the active substance is released to its surroundings within a maximum period of 1 minute. The active substance can, for example, be released in the form of particles and can then become effective by dissolution in the course of a longer period of time;

Low molecular weight: Substances with a molecular weight less than 5000 Da, and preferably <2000 Da, and particularly preferred <1000 Da;

Hydrophilic/hydrophilised balloon membrane: hydrophilic membranes consisting of materials which can be wetted with water or with hydrophilic solvents; hydrophilised membranes are membranes made out nylon, for example, whose surfaces were changed by subsequent treatment into a state that can be wetted with water or other hydrophilic solvents. Hydrophilic or hydrophilised membranes are not to be confused with membranes which are provided with an additional hydrophilic layer;

Hydrophilically-coated balloon membrane: A membrane, which contains an additionally applied layer, which can itself be wetted with water;

Open on the surface: Pharmaceuticals or additives which are not incorporated into the balloon membrane or which are not incorporated into any layers that are firmly attached to the balloon membrane. For example, they are not incorporated in any polymeric water-insoluble coatings particularly any hydrogels that may not become detached. Open on the surface includes coatings which become covered by the folds in the balloon membrane when it is in its folded condition;

Good adhesion: Folded balloon catheters (Orbus IX, Bavaria Medizin Technologie, Oberpfaffenhofen, Germany, SeQent, BBraun, Melsungen, Germany balloon size 3.5 mm diameter, 20 mm length or comparable products from other manufacturers) are coated in the folded state with 3 µg active substance/mm$^2$ according to the dosing procedure described below. The balloons are expanded when dry and shaken for 5 seconds in a glass vessel. More than 75% of the dose remains on the balloon;

Highly volatile: Solvents with a boiling point below 300° C., and preferably below 160° C., with below 100° C. being particularly preferred.

DESCRIPTION OF THE INVENTION

The invention has the purpose of making improved medicinal products available e.g. balloon catheters which enable reliable localised treatment of diseased tissue to be carried out, new applications to be developed and to facilitate the use of hydrophilic active substances that are easily soluble in water.

It is a particular purpose of this present invention to prepare a balloon catheter which does not lead to a stretching or overstretching of the vessel and yet still releases a sufficient quantity of the active substance for the treatment or prophylaxis of diseases of the vascular wall.

This purpose is achieved by the independent patent claims of this present invention. Further advantageous embodiments are to be found in the description, the examples and in the dependent claims. Novel balloon catheters using a special method of construction are therefore disclosed together with methods for coating balloon catheters which are provided in a sufficiently detailed form.

Active Substances and Additives

The following are preferred as active substances:
antiproliferative, antiinflammatory, antiphlogistic, antihyperplastic, antineoplastic, antimitotic, cytostatic, cytotoxic, antiangiogenic, antirestenotic, microtubule inhibiting, antimigrative or antithrombotic active substances.

Examples of antiproliferative, antiinflammatory, antiphlogistic, antihyperplastic, antineoplastic, antimitotic, cytostatic, cytotoxic, antiangiogenic, antirestenotic, microtubule inhibiting, antimigrative or antithrombotic active substances are:

abciximab, acemetacin, acetylvismione B, aclarubicin, ademetionine, adriamycin, aescin, afromoson, akagerine, aldesleukin, amidorone, aminoglutethemide, amsacrine, anakinra, anastrozole, anemonin, anopterine, antimycotics, antithrombotics, apocymarin, argatroban, aristolactam-AII, aristolochic acid, arsenic trioxide and other compounds containing arsenic, ascomycin, asparaginase, aspirin, atorvastatin, auranofin, azathioprine, azithromycin, baccatine, bafilomycin, basiliximab, bendamustine, benzocaine, berberine, betulin, betulinic acid, bilobol, biolimus, bisparthenolidine, bleomycin, bombrestatin, boswellic acids and their derivatives, bruceanoles A, B and C, bryophyllin A, busulfan, antithrombin, bivalirudin, cadherins, camptothecin, capecitabine, o-carbamoylphenoxyacetic acid, carboplatin, carmustine, celecoxib, cepharanthin, cerivastatin, CETP inhibitors, chlorambucil, chloroquine phosphate, cictoxin, ciprofloxacin, cisplatin, cladribine, clarithromycin, colchicine, concanamycin, coumadin, C-Type natriuretic peptide (CNP), cudraisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, dunaimycin, epirubicin, epothilone A and B, erythromycine, estramustine, etoposide, everolimus, filgrastim, fluroblastin, fluvastatin, fludarabine, fludarabin-5'-dihydrogenphosphate, fluorouracil, folimycin, fosfestrol, gemcitabine, ghalakinoside, ginkgol, ginkgolic acid, glycoside 1a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, bismuth and bismuth compounds or chelates, irinotecan, topotecan, hydroxycarbamide, miltefosine, pentostatine, pegaspargase, exemestane, letrozole, formestane, SMC proliferation inhibitor-2ω, mitoxantrone, mycophenolate mofetil, c-myc antisense, b-myc antisense, β-lapachone, podophyllotoxin, podophyllic acid 2-ethylhydrazide, molgramostim (rhuGM-CSF), peginterferon α-2b, lanograstim (r-HuG-CSF), macrogol, selectin (cytokin antagonist), cytokin inhibitors, COX-2 inhibitor, NFkB, angiopeptin, monoclonal antibodies which inhibit muscle cell proliferation, bFGF antagonists, probucol, prostaglandins, 1-hydroxy-11-methoxycanthin-6-one, scopolectin, NO donors, pentaerythritol tetranitrate, syndnoimines, S-nitrosoderivatives, tamoxifen, staurosporine, β-oestradiol, α-oestradiol, oestriol, oestrone, ethinyloestradiol, medroxyprogesterone, oestradiol cypionates, oestradiol benzoates, tranilast, kamebakaurin and other terpenoids, which are used in the treatment of cancer, verapamil, tyrosine kinase inhibitors (tyrphostins), paclitaxel, paclitaxel derivatives, 6-α-hydroxy paclitaxel, 2'-succinylpaclitaxel, 2'-succinylpaclitaxeltriethanolamine, 2'-glutarylpaclitaxel, 2'-glutarylpaclitaxeltriethanolamine, 2'-O-ester of paclitaxel with N-(dimethylaminoethyl)glutamide, 2'-O-ester of paclitaxel with N-(dimethylaminoethyl)glutamidhydrochloride, taxotere, carbon suboxides (MCS), macrocyclic oligomers of carbon suboxide, mofebutazone, lonazolac, lidocaine, ketoprofen, mefenamic acid, piroxicam, meloxicam, penicillamine, hydroxychloroquine, sodium aurothiomalate, oxaceprol, β-sitosterin, myrtecaine, polidocanol, nonivamide, levomenthol, ellipticine, D-24851 (Calbiochem), colcemid, cytochalasin A-E, indanocine, nocadazole, S 100 protein, bacitracin, vitronectin receptor antagonists, azelastine, guanidyl cyclase stimulator tissue inhibitor of metal proteinase 1 and 2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active substances from the group of antibiotics such as cefadroxil, cefazolin, cefaclor, cefotixin, tobramycin, gentamycin, penicillins such as dicloxacillin, oxacillin, sulfonamides, metronidazole, enoxoparin, desulphated and N-reacetylated heparin, tissue plasminogen activator, GpIIb/IIIa platelet membrane receptor, factor Xa inhibitor antibodies, heparin, hirudin, r-hirudin, PPACK, protamine, prourokinase, streptokinase, warfarin, urokinase, vasodilators such as dipyramidol, trapidil, nitroprussides, PDGF antagonists such as triazolopyrimidine and seramine, ACE inhibitors such as captopril, cilazapril, lisinopril, enalapril, losartan, thioprotease inhibitors, prostacyclin, vapiprost, interferon a, β and γ, histamine antagonists, serotonin blockers, apoptosis inhibitors, apoptosis regulators such as p65, NF-kB or Bcl-xL antisense oligonucleotides, halofuginone, nifedipine, tocopherol tranilast, molsidomine, tea polyphenols, epicatechin gallate, epigallocatechin gallate, leflunomide, etanercept, sulfasalazine, etoposide, dicloxacillin, tetracycline, triamcinolone, mutamycin, procainimide, retinoic acid, quinidine, disopyramide, flecainide, propafenone, sotolol, naturally and synthetically obtained steroids such as inotodiol, maquiroside A, ghalakinoside, mansonine, strebloside, hydrocortisone, betamethasone, dexamethasone, non-steroidal substances (NSAIDS) such as fenoporfen, ibuprofen, indomethacin, naproxen, phenylbutazone and other antiviral agents such as acyclovir, ganciclovir and zidovudin, clotrimazole, flucytosine, griseofulvin, ketoconazole, miconazole, nystatin, terbinafine, antiprozoal agents such as chloroquine, mefloquine, quinine, furthermore natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceantinoside C, yadanziosides N, and P, isodeoxyelephantopin, tomenphantopin A and B, coronarin A, B, C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterin, protoanemonin, cheliburin chloride, sinococuline A and B, dihydronitidine, nitidine chloride, 12-beta-hydroxypregnadien-3,20-dione, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, maytansin, lycoridicin, margetine, pancratistatin, liriodenine, bisparthenolidine, oxoushinsunine, periplocoside A, ursolic acid, deoxypsorospermin, psycorubin, ricin A, sanguinarine, manu wheat acid, methylsorbifolin, sphatheliachromen, stizophyllin, mansonine, strebloside, dihydrousambaraensine, hydroxyusambarine, strychnopentamine, strychnophylline, usambarine, usambarensine, liriodenine, oxoushinsunine, daphnoretin, lariciresinol, methoxylariciresinol, syringaresinol, sirolimus (rapamycin), rapamycin combined with arsenic or with compounds of arsenic or with complexes containing arsenic, somatostatin, tacrolimus, roxithromycin, troleandomycin, simvastatin, rosuvastatin, vinblastine, vincristine, vindesine, thalidomide, teniposide, vinorelbine, trofosfamide, treosulfan, tremozolomide, thiotepa, tretinoin, spiramycin, umbelliferone, desacetylvismione A, vismione A and B, zeorin, fasudil.

Preferred active substances that can be applied to the catheter balloon are paclitaxel and other taxanes, rapamycin and other mTOR (mammalian target of rapamycin) inhibitors, methotrexic acid, arsenic or arsenic compounds, bismuth or bismuth compounds or thalidomide.

In a further preferred embodiment at least one active substance is present as a neutral substance which is sparingly soluble in water, as a salt which is sparingly soluble in water or as an acid which is sparingly soluble in water.

As hydrophilic additives the following are used: preferably volatile hydrophilic solvents or hydrophilic solvent mixtures as well as non-volatile substances which do not have any intended biological effects in the form in which they are administered such as sugar, sugar alcohols, amino acids, fats, inorganic or organic salts and/or contrast media or dyes that are suitable for intravascular application.

Preferred additives are ascorbic acid, urea, polyethylene glycol 8000 and, despite their poor solubility in water, also triglycerides in particular triglycerides that are solid at room temperature such as trimyristin.

Balloon Catheter for Coating

In the patent specifications mentioned above then usually smooth walled balloon catheters for percutaneous transluminal angioplasty are described, consisting of various materials such as nylon, PEBAX, polyethylene and many others which are disclosed in DE 10 2004 046 244 and in other patent specifications or there are balloon catheters provided with grooves or with pores, in which the active substance is placed, or there are balloon catheters with texturised and roughened membranes. The aim of the structural changes with regard to an increase in surface area is to increase the loading with active substances or to improve the adhesion of the active substances to the balloon. Furthermore in WO 2004/006976 balloons are described coated with an additional hydrophilic layer. The balloons of these catheters are expandable up to a predetermined size and should preferably be pressure resistant in order to be able expand stenotic arteries back to their original diameter.

The texturising of the surface does however have the disadvantage of delaying the release of the active substance when the balloon is expanded in the vessels. In their expanded state the balloons completely block the flow of blood through the vessels being treated. A blockage of the flow of blood is only tolerated for a very short period of time, particularly in the coronary arteries. The effective dose must be released during this time. Every delay in the detachment of at least one active substance from the balloon membrane is a disadvantage.

Surprisingly it was found that hydrophilic or hydrophilised balloon membranes could be reproducibly and evenly coated with active substances. In addition a wide range of solvents were suitable for coating and that a minimum of one active substance adhered to the balloon membrane perfectly. This is particularly true for the case when the balloons are coated in a ready folded condition. Hydrophilic balloon membranes are known and are used to improve the ability of the catheter to slide before the balloon is expanded.

This present invention therefore concerns a balloon catheter that includes a catheter balloon with a catheter membrane where the balloon membrane is hydrophilic or hydrophilised and/or the surface of the balloon membrane has a hydrophilic coating. This hydrophilic coating preferably adheres strongly to the surface of the balloon i.e. it is securely attached to the surface of the balloon and does not become detached when the balloon is dilatated.

This present invention also concerns balloon catheters that include a catheter balloon with a hydrophilic or hydrophilised balloon membrane where the balloon membrane is coated with at least one active substance lying open on its surface which is coated in such a way that at least one substance is immediately released when the catheter balloon is expanded. Furthermore the catheter balloon can additionally be coated with additives if required.

The hydrophilic surface of the balloon, or the hydrophilically coated surface of the balloon, or the surface of the balloon membrane that is provided with a firmly adhering hydrophilic coating is preferably coated with at least one hydrophilic active substance, or with at least one hydrophilic active substance together with at least one hydrophilic additive.

Preferred catheter balloons according to the invention therefore demonstrate two coatings, a lower hydrophilic coating which adheres securely and an outer detachable coating made from one active substance or from a mixture containing at least one active substance.

It is furthermore preferred when the generally lipophilic balloon surface is treated with active oxygen to make it hydrophilic. The hydrophilic membrane or more specifically the hydrophilic surface of the balloon membrane (i.e. the hydrophilic surface of the balloon) can be produced by a hydrophilic coating on lipophilic balloon membranes (or the lipophilic surfaces of the balloon) or by being chemically changed (e.g. by reaction with active oxygen) to a lipophilic membrane. This latter method is preferred for coating purposes.

Hydrophilic catheter balloons can be coated with simple processes which use a coating mixture, such as immersion, to produce coatings that are very reproducible, so that the active substance content on the catheter balloon which is coated with at least one active substance demonstrates an average standard deviation of less than 20%, preferably less than 15%, more preferably less than 10% and even more preferably less than 5%.

In a further preferred embodiment the balloon membrane or the hydrophilic balloon membrane or the hydrophilically coated balloon membrane is coated with at least one hydrophilic active substance which if required is present in the mixture with at least one slightly water soluble additive. This embodiment offers the advantage that the slightly water soluble additive inhibits premature detachment of the active substance.

By coating with active substances or additives the improved ability of the hydrophilic balloons to slide is lost, at least when the coating is also situated on the outside of the non-expanded balloon. Hydrophilic balloons have the disadvantage that when they are expanded in constricted arteries they slip out of the desired position more easily. According to our own observations this disadvantage is largely overcome by coating using pharmaceuticals and matrix substances, because the coating that is then released into the surrounding medium noticeably increases the friction between the balloon and the arterial wall.

The usual angioplasty balloons should not overstretch the vessels. They therefore achieve a certain diameter with a low pressure which cannot significantly be increased by increasing the pressure.

A further useful modification to the balloon membrane concerns its mechanical properties. To transfer the active substance to the vascular wall without overstretching it, membranes are selected which are soft or compliant and which are expandable at low pressure, or which significantly exceed the diameter of the vessels.

Significantly exceed means that the diameter of the balloon preferably exceeds the reference diameter of the vessel by at least 20% and more preferably by more than 30% where the balloon preferably is stretched with not more than around 2000 hPa. These balloons are not intended to significantly widen the vascular lumen by means of pressure on the vascular wall. A significant widening of the lumen is specifically the removal of an occlusion or a high grades stenosis, or the widening of the lumen by more than 30% of the reference diameter of the vessel. The membrane properties can be achieved by the informed selection by an expert of the composition of the membrane and/or the strength of its walls and the folding. The balloons can have a comparatively low bursting pressure e.g. equal to or less than 10,000 hPa (9.87 atmospheres; [1 atmosphere=1013 hPa]), preferably equal to or less than 5000 hPa (4.93 atmospheres), because they cannot be expanded with high pressures. Preferred expansion pressures are preferably below 4000 hPa (3.95 atmospheres), more preferred under 2000 hPa (1.97 atmospheres) and even more preferred is under 1000 hPa (0.97 atmospheres) above normal pressure. Pressures between 2000 hPa (1.97 atmospheres) and 200 hPa (0.20 atmospheres) above normal are particularly preferred. Catheters for the treatment of arteries, veins or dialysis shunts preferably have a diameter to length ratio of less than 0.2, and more preferable is a diameter to length ratio of less than 0.1.

The described balloons should not be confused with balloons which, for example, are made from silicon or latex, are generally more spherical in shape and are used to anchor catheters in cavities such as the bladder without completely filling the cavity concerned.

According to the invention balloon catheters are also preferred which already achieve their maximum diameters in their expanded condition at low pressures and which still possess a certain flexibility in order to adapt to an uneven vascular wall. It is therefore preferred when after it has been completely unfolded using an increase in pressure that the radius of the catheter balloon increases by more than 15%, preferably more than 30% and even more preferably by more than 60%. The increase in pressure takes place by introducing a gas (e.g. carbon dioxide) or a fluid, for example a contrast medium, into the catheter balloon in the usual manner.

Furthermore balloon catheters are preferred in which, after they have been completely unfolded by increasing the pressure inside the catheter balloon, the radius of the catheter balloons increases by more than 15%, more preferably by more than 30% and even more preferably by more than 60%.

A further embodiment of this present invention deals with a balloon catheter with at least one active substance open on the surface which is immediately released when the balloon is expanded where after the balloon has completely unfolded by increasing the pressure inside the catheter balloon, the radius of the catheter balloons increases by more than 15%, more preferably by more than 30% and even more preferably by more than 60%.

The active substance or active substances and if required further additives adhere to the balloon membrane and/or despite its lack of rigidity are surprisingly well protected from being prematurely detached because of its structure or because of the folding of the ready to use balloon. The structure of the balloon membrane in the contracted or non-operational position i.e. without the balloon membrane being expanded can contain recesses, depressions and embossments or folds which become flattened during expansion under low pressure because of the flexibility and elasticity of the membrane. The use of these balloons is particularly advantageous in the treatment of changes to the vessels which do not significantly restrict the flow of blood i.e. they constrict the free vascular lumen by less than 50%. They permit the treatment of less pressure resistant vessels, because at a low pressure they are able to position themselves against an irregular vascular wall. Balloon catheters according to this invention are particularly suitable for the treatment and prophylaxis of vascular diseases and in particular for inflammatory vascular changes, vulnerable plaque, sections of vessels that had previously been treated either surgically or mechanically, extensive lesions without the necessity of (a renewed) stretching. It is also suitable for narrow vessels which are inaccessible to stents. Balloon catheters according to this invention are pre-eminently suitable for the treatment of changes to the vascular wall which do not restrict the flow of blood.

Coating

One of the previously unsolved problems is to distribute an acceptably accurate dose of the active substance sufficiently evenly on the surface of the balloon. In the administration of pharmaceutical products there are stringent requirements concerning the accuracy of the dosage of the pharmaceutical form, which is, in this case, the coating of the balloon. While accurate dosing procedures are well known in pharmacy, in most pharmaceutical applications there is no necessity to distribute active substances evenly across a surface.

In addition the usual dosing apparatus used in pharmacy and biochemistry mainly operate using aqueous solutions where the vapour pressure of the dose does not significantly cause any difficulties.

In the patent specifications described below there are some vague indications of how this problem could be solved. The significance of the problem is however not recognized. In particular no processes were described which would enable the expert to coat balloons in an economical and reproducible manner so that the products are reliably effective in releasing the pharmaceuticals rapidly and completely at the site of pharmacological action.

The coating processes disclosed in EP 1 372 737 A and WO 2004/028582 A involving the repeated immersion of ordinary ready-to-use balloons (when folded) in less viscous solutions of lipophilic pharmaceutical products and suitable additives have produced a dose on the balloon which in the first instance was sufficiently reproducible for medical use. One important insight was that despite the inhomogeneous distribution of the active substances on the balloons in a radial direction, which was caused by the folding of the balloon, on expansion of the balloon an even distribution of at least one active substance is produced on the balloon (Scheller B, Speck U, Böhm M. Prevention of restenosis—is angioplasty the answer? Heart 2007; 93:539-541). A series of disadvantages was however evident in their routine use for production.

The process is inconvenient and time consuming because it requires repeated immersions, with drying processes taking place in between the immersions. The amount of active substance adhering to the balloons is determined by a number of not always controllable factors. While the coating of almost identical balloons from one batch was largely reproducible to a satisfactory standard, this did not always apply to batches from different production runs. A further problem that is difficult to solve in an immersion process is the longitudinal distribution of the active substances. In particular there is the possibility that the proximal section of the balloon is not sufficiently well coated. Finally measures are necessary in the process mentioned to prevent the penetration of the less viscous solution into the central lumen of the catheter. The remaining previously known coating processes provide even more unfavourable results. A coating of expanded balloons had the result that the balloons had to be folded with the coating in place. From a consideration of the dosage applied this is only realisable in any way that is reasonably free from losses when the coating adheres firmly. A coating that adheres firmly is not released sufficiently during the short period of time when there is contact between the balloon membrane and the vascular wall. When folded balloons are coated by spraying the active substance is located only on the surface of the balloon which leads to increased losses when the balloon catheter is introduced through the insertion sheath, through the guide catheters and through the preceding blood vessels. Spraying, brushing and pipetting ensure neither a reproducible dose that can be accurately predetermined nor the even distribution of an active substance on the catheters. With the usual pipettes the exact measurement of the very small volumes that are necessary from the preferred highly volatile solvents is just as difficult as the even distribution of solution onto the balloon. The advantage of the process described in WO 2007/090385 is the placing of the active substances underneath the folds of the balloon.

A process according to the invention for coating medicinal products or parts thereof (e.g. balloons at the distal ends of catheters) includes the following stages:

a) preparation of a catheter balloon,
b) preparation of a micro-dosing unit containing a coating mixture which does not come into contact with a gaseous phase,
c) uniform coating of the catheter balloon with the coating mixture using the micro-dosing unit and without any losses.

In the coating mixture there is generally a coating solution or a coating fluid where a gel, a suspension, emulsion, dispersion or slurry can however also be used.

During the coating it is important that the solvent from the coating solution cannot evaporate before it is applied to the balloon. The solvent must not be in contact with any gaseous phase, whose volume could affect the dose that is administered.

The catheter balloon is preferably mounted horizontally during the coating stage and is rotated about its longitudinal axis while the micro-dosing unit moves to and fro along the longitudinal axis of the catheter balloon in order to achieve the complete coating of the folded or not completely unfolded balloon.

Figure 3:
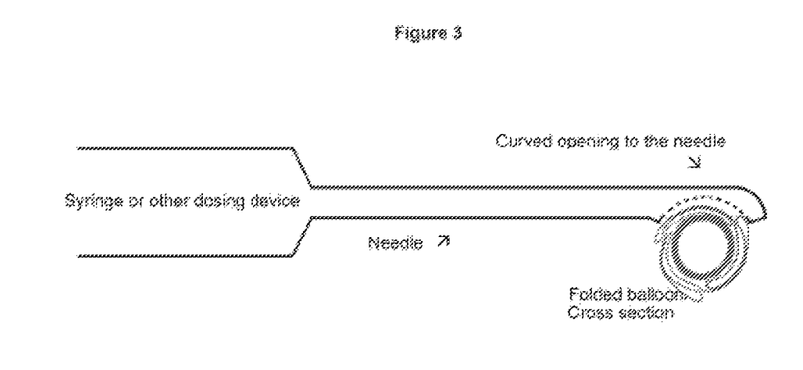
FIG. 3 shows an exemplary micro-dosing apparatus of the instant invention.

A syringe (see FIG. 3) a cannula, a tube or some other device can be used as a micro-dosing unit that is precise enough for the administration of the necessary small amounts onto the catheter balloon and which does not damage the catheter balloon during the coating and preferably does not touch it at all.

It is preferable that highly volatile solvents or chlorine compounds or fluorine compounds with a boiling point below 300° C. are used, and more preferably with a boiling point below 100° C. are used as solvents for the coating mixture. Furthermore hydrophilic solvents or mixtures of at least one solvent or hydrophilic solvent with water can be used.

The balloons are preferably coated in their folded form, but can however also be coated in any other form using a suitably adapted device.

In order to achieve an even coating, the entire membrane from proximal to distal including all the folds should be simultaneously wetted with the coating mixture during the coating process. This should however take place without any dripping of the coating mixture.

A gel can also be used as the coating mixture. Here at least one of the active substances can itself function as the gelling agent or take part in gel formation. The active substance itself can function as a gelling agent if a gel like coating mixture is obtained, without any further gel forming substances being present beside the active substance.

In addition it is preferred that at least one active substance is applied to the catheter balloon in a form which is sparingly soluble in water.

As an alternative at least one active substance that may be readily soluble in water i.e. is hydrophilic can be changed into a sparingly soluble form after it has been applied to the balloon. This can occur, for example, by complexing with cyclodextrins or by salt formation. The manufacture of a salt that is sparingly soluble in water and the selection of a counterion or complex forming agent are part of the standard knowledge possessed by an expert and can be determined by simple tests of solubility.

A preferred embodiment of the coating process according to the invention is described in the following section and includes:

A) The preparation:
1) selected balloon catheters or suitable components that contain the balloon, where the balloon is preferably in the folded condition or in a condition with preformed folds, which are not however pressed tightly together.
2) a device to hold the balloon preferably in a horizontal position where the balloon in a preferred embodiment can be rotated around its longitudinal axis
3) a device for measuring microvolumes for the administration of solutions preferably containing highly volatile organic solvents in which the volume to be administered does not come into contact with any gaseous phase which could affect the dose administered.
4) a component designed to transfer the liquid from the volume measuring device to the balloon.
5) a solution containing at least one active substance and optionally one or more additives.

B) The work stages:
1) calculation of the necessary volume for the coating of the balloon at the desired dosage using the known surface of the balloon in $mm^2$ and the concentration of the active substance in the substance
2) introduction of the catheter or the part of the catheter that holds the balloon into the mounting
3) calibration of the volume measuring device for the calculated volume of the solvent being used
4) filling of the volume measuring device with the coating solution which takes place without any bubbles of gas being present
5) continual slow rotation of the balloon about its longitudinal axis
6) positioning of the component for transferring liquid with the opening through which the solution exits either located on the balloon or just above the balloon, or directly below the balloon or to one side of the balloon
7) transfer of the intended volume of coating solution onto the balloon while the component for transferring liquid is moved with a steady speed backwards and forwards along the cylindrical part of the balloon in the direction of the longitudinal axis. The speed of transfer of the solution is preferably to be adjusted so that all parts of the balloon are wetted with the liquid at the same time without any drops forming on the balloon which could fall off.

The volume measuring device ensures an accurate dose on the balloon independent of the balloon material and its surface structure (smooth or texturised), independent of whether it is tightly folded or loosely folded or whether it is partially or completely expanded, independent of the size and the type of balloon and of the individual batches of balloons used. The movement of both the balloon and the component for transferring liquid combined with the complete wetting of the balloon using the coating solution does however effect a surprisingly uniform distribution even on long stretched balloons.

After coating the balloons can under suitable conditions be ready folded and/or dried, stents can be assembled and the catheters packed and sterilised in the usual way.

The principle described above for coating can be realised by an expert using various items of equipment and different devices in various ways which can be matched to the needs of the objects that require coating. They are characterized by the accuracy of the dosage and the placement of the dose, the uniformity of distribution of the coating on the surface of the area to be coated including the penetration of the mixture into the folds and other not readily accessible structures. It is simple and cost-effective to manipulate, because the amount of material needed and the amount of time needed are both minimal; the process is also easy to control and can be automated. In particular the loss of the coating mixture in containers and as a result of any unwanted distribution of the mixture onto the medicinal product or onto its surroundings is avoided. Any change in the coating mixture before the application to the medicinal product by premature evaporation solvents is impossible.

Accelerated Dissolution and Detachment of Lipophilic Active Substances

A series of solvents for the coating of medicinal products with pharmaceuticals are described in EP 1 372 737 A and WO 2004/028582 A, in U.S. Pat. No. 6,306,166 and in other specifications. It was surprisingly found that lipophilic pharmaceutical products, for example not only paclitaxel and other taxanes, but also rapamycin and related substances become particularly easily detached from the balloon surface in aqueous media, blood or tissue and go into solution when the coating of the medicinal products is carried out with solutions of substances in chloroform or dichloromethane or other highly volatile chlorine and fluorine compounds.

Further suitable measures for accelerating the detachment of lipophilic active substances and/or active substances that are sparingly soluble in water are the use of volatile hydrophilic organic solvents particularly methanol, ethanol, propanol, formic acid, acetic acid, tetrahydrofuran (THF), acetone, 3-pentanone, esters of carboxylic acids in particular methyl formate, ethyl formate, methyl acetate, ethyl acetate etc. and mixtures of these substances with water. One particularly preferred form of coating with, for example, paclitaxel does without any additional coating of the original balloon membrane with other polymers, hydrogels or other carrier layers for pharmaceutical products, for all additives and for complex mixtures of solvents. Such coatings have previously proved to be largely ineffective (Scheller B, Speck U, Abramjuk C, Bernhardt U, Böhm M, Nickenig G: Paclitaxel balloon coating—a novel method for prevention and therapy of restenosis. Circulation 2004; 110: 810-814, WO 2004/028582, example 7; Cremers B, Biedermann M, Mahnkopf D, Böhm M, Scheller B. Paclitaxel-beschichtete PTCA-Katheter: Gibt es Unterschiede? Einfluss von PACCOCATH®-und DIOR®-Ballonkathetem auf die Neointimaproliferation an Schweinekoronarien (Paclitaxel coated PTCA catheters: are there any differences? The effect of PACCOCATH® and DIOR® balloon catheters on neointimal proliferation in coronary arteries in pigs) Clin Res Cardiol 2008; 97-Suppl 1: V1742).

Surprisingly the crystal structure and the adhesion of paclitaxel to the balloon membrane is able to be very precisely controlled by the addition of a small amounts of water to a solution of paclitaxel in, for example, isopropanol, tetrahydrofuran, dimethylformamide or acetic acid or mixtures containing these solvents. Preferred solvents are (a) those that lead to a very strong adhesion of paclitaxel to the balloon membrane and (b) those that dissolve at least one percent by volume of water at room temperature. From these simple solvent mixtures crystals of the active substances are formed without any technological outlay. In one specific case paclitaxel crystals are formed which adhere strongly to the folded balloon. When the balloon is expanded, for example in constricted arteries, they are almost completely detached and are to a large extent transferred to the tissue.

The crystals slowly dissolve there—as is known from pharmacy—and over a certain period of time this ensures that there is an effective concentration of pharmaceutical product. The application to the balloon is significantly more straightforward using the dosing process described above. With regard to the dosage it is more accurate than that described in WO 2007/090385. Not having a matrix substance has the great advantage that the compatibility of the matrix with the active substance, its long term stability, its effect on the balloon membrane and its biological tolerance do not have to be tested. Additives can affect the adhesion of preassembled stents, for example when the adhesion is reduced and the stent is prematurely lost or when the adhesion is increased and the stent is not released from the balloon after expansion; in both cases the patients are endangered. The reduced load on the balloon by not having an additive is also advantageous because the additionally applied substance makes the necessary tight folding of the balloon more difficult. A smaller external diameter is necessary for the balloons to pass through narrow stenoses.

Further embodiments according to this invention concern catheter balloons with a smooth walled membrane that is coated with an active substance dissolved in an organic solvent which contains at least 1% water, preferably at least 10% water, which is then dried and sterilised and in which the active substance is present in a crystalline form. Here it is preferred that the catheter balloons with smooth walled balloon membranes are coated in the folded condition.

A further preferred embodiment of this present invention concerns the balloon catheter in which the balloon membrane of the catheter balloon that is coated with an active substance dissolved in an organic solvent which contains at least 1% water, preferably at least 10% water, which is then dried and sterilised and in which the active substance is present in a crystalline form.

A further preferred embodiment of this present invention therefore concerns the balloon catheter where the balloon membrane of the catheter balloon is smooth walled and is coated with paclitaxel crystals that lie open on the surface, without any additives and coated in a manner in which when the folded balloon is introduced into an artery at least 70% of the paclitaxel, preferably at least 80% and more preferably at least 90% of the paclitaxel remains adhering to it and where when the catheter balloon is expanded in a restricted artery it is immediately released.

Soluble, water-soluble or micro-particular matrix substances can be added to the liquid preparations for coating, as is already known, where the particular matrix substance can also be the active substance itself. The selection of a suitable additive is in most cases dependent on the active substance, the solvent and the surfaces of the balloons. Examples of suitable additives that encourage detachment of the coating are ascorbic acid, urea and polyethylene glycol preferably in the molecular weight range from around 5000 to 20,000 Da. On account of the unfavourable effect of the loading on the diameter and flexibility of the coated balloon the total loading of the balloon (active substance and additive) i.e. the total dose of all non-volatile components applied to the balloon membrane should preferably be below 10 μg/mm² and more preferably below 5 μg/mm² balloon surface in the expanded state and additives should be applied at a rate of preferably below 1 μg/mm² balloon surface and more preferably below 0.3 μg/mm².

The present invention further concerns a balloon catheter in which the balloon membrane of the catheter balloon is coated with at least one active substance lying open on the surface and either ascorbic acid or urea or a sold triglyceride at room temperature like trimyristin or polyethylene glycol in the molecular weight range from 800 to 20,000 daltons, or any preferred mixture of the these in a manner in which at least one active substance is immediately released when the catheter balloon is expanded.

Water Soluble and/or Hydrophilic Substances

Previously there were two different classes of compounds for the localized treatment and prophylaxis of arterial diseases: '. . . hydrophobic drugs, which are retained within tissue and have dramatic effects, and hydrophilic drugs, which are rapidly cleared and ineffective' (Levin A D, Vukmirovic N, Hwang C-W, Edelman E R. Specific binding to intracellular proteins determines arterial transport properties for rapamycin and paclitaxel. PNAS 2004; 101:9463-9467).

In U.S. Pat. No. 6,306,166 it was explicitly stated that it was mainly active substances that were insoluble in water that were selected for use in coating. For example the coating of stents with insufficiently lipophilic substances had proved ineffective for restenosis prophylaxis (Muni N I et al. Am Heart J 2005; 149:415-433; Kiesz R S et al. Circulation 2001; 103:26-31; Kutryk M J B et al. J Am Coll Cardiol 2002; 39:281-7). Huang y et al. Am J Cardiol reported about a slight inhibition of neointimal proliferation using stents coated with methotrexate which slowly released the active substance from a polymer. The use of methotrexate for coating catheter balloons is disproportionately more difficult, because the water soluble active substance dissolves quickly, even before the balloon has reached the stenosis in the blood vessel. For arsenic trioxide efficacy after the slow release from a polymer matrix was also described (Yang W, Ge J, Liu H et al. Cardiovascular Research 2006; 72:483-493). The restriction of pharmaceutical products to lipophilic substances places undesirable limits on selection with regard to efficacy, activity profile and availability. It is indeed from the water soluble, less lipophilic substances that extraordinarily effective active substances can be found. Despite their completely different physicochemical and pharmokinetic properties it was surprisingly found that like lipophilic pharmaceutical products water soluble and/or hydrophilic active substances could cause long lasting effects from an exposure of cells lasting only a short period of time. Surprisingly there was no need to compensate for the rapid dilution of these substances by means of sustained release from a reservoir implanted for long term use.

Problems that are difficult to solve arise from the use of hydrophilic, mainly readily water soluble pharmaceuticals for administration by means of coated medicinal products, particularly balloon catheters. Sparingly water soluble substances such as paclitaxel or rapamycin and its derivatives largely continue to adhere to the surface of the coated medicinal products when they are placed in insertion sheaths, in guide catheters and in the blood; they only become detached from the vascular wall under mechanical stress e.g. by the expansion of the balloon and by rubbing against the vascular wall and if necessary they can be dissolved in the presence of proteins and membrane lipids Hydrophilic substances on the other hand dissolve on the first contact with water or with blood and are lost to a great extent before they reach the targeted location. Hydrophilic substances therefore generally need protective measures to be taken to inhibit their release when they are used during the short time that elapses between the first contact of the sterilized medicinal product with aqueous liquids (with blood for example) before arriving at the targeted location and the actual arrival at the targeted location itself.

These measures should not be confused with formulations which effect a delayed release of the active substance at the site of pharmacological action in order to ensure that the effects last over a longer period of time. The release of hydrophilic, water soluble active substances should take place immediately the active substance has reached the site of pharmacological action and should not take place earlier.

A surprising anomaly is shown by arsenic trioxide despite its hydrophilic character. It can be applied on the balloon surface as a solution, but does however adhere strongly to the membrane after drying and is almost completely released on expansion.

The problem with hydrophilic and/or water soluble active substances begins with the application onto the surface of the medicinal products. Many of these surfaces, in particular the catheters which are usually used only allow themselves to not be wetted, or else to be very unevenly wetted by aqueous or other hydrophilic solvents. A further significant property is the adhesion of the coating to the surface of the medicinal product or specifically the balloon membrane. The evenness of distribution of the coating and its adhesive properties are surprisingly clearly influenced by slight changes to the surface. Surfaces that are treated with activated oxygen ('plasma') therefore not only demonstrate an even distribution but in particular they also show very good adhesion to the folded membrane and very good detachment of the coating from the balloon when it is expanded. Similar results are obtained with hydrophilically derivatised or hydrophilically coated membranes.

Water is only suitable for use as the solvent for the application of hydrophilic and/or water soluble active substances to a limited extent. Relatively hydrophilic organic solvents such as methanol, ethanol, propanol, isopropanol, dimethylsulfoxide, acetone, formic acid, acetic acid, ammonia, tetrahydrofuran, dimethylformamide, dimethylacetamide etc., mixtures of these solvents with each other and mixtures of these solvents with water where the pH of the solution can be adjusted using acids and bases. It is preferable that solvents are to be removed before use. The solvents are evaporated as far as possible before the use of the medicinal products, if necessary using increased temperatures and a reduced pressure.

The hydrophilic and/or water soluble substances can be dissolved as such or in the form of salts. In the case of anthracyclines, and particularly doxorubicin, viscous solutions, which are surprisingly well suited to the coating of surfaces, can be manufactured using a suitable selection of concentration, ion concentration, preferably the sodium ion concentration, and pH (Hayakawa E, Furuya K, Kuroda T, Moriyama M, Kondo A. Viscosity study on the self-association of doxorubicin in aqueous solution. Chem. Pharm Bull 1991; 39:1282-1286). Although these solutions can contain water as the only solvent, very uniform coatings can be obtained even when the membranes are rather lipophilic as used in the usual balloon catheters.

All the coatings mentioned above are applied according to one of the usual processes: by immersion, by spraying, by brushing or by means of a volume measuring device, preferably according to the process described above using a volume measuring device. In the case of balloon catheters the balloons are coated when expanded, when folded or in some intermediate state.

A further possibility for coating with hydrophilic and/or water soluble substances is that the substances are not applied to the surface in the form of a solution. Hydrophilic and/or water soluble substances can for example be applied in the form of microparticles, or nanoparticles in liquids in which they are only slightly soluble or they are precipitated from liquids in which they are soluble. This permits the use of lipophilic organic solvents and the addition of lipophilic additives in combination with hydrophilic and/or water soluble substances. Premature detachment of the coating is prevented by coating the surfaces with preformed particles and if required by the addition of lipophilic additives in lipophilic solvents.

Many hydrophilic and/or water soluble substances contain functional groups which can become electrically charged. They can be soluble in organic solvents when they are not electrically charged and be used for coating in this form. They can form readily soluble or sparingly soluble salts. One preferred possibility for coating medicinal products is the use of sparingly soluble salts of hydrophilic and/or water soluble substances. In this way premature detachment is avoided following contact with physiological solutions which are, for example, used to wet the catheters or else following contact with blood in insertion sheaths, guide catheters or else direct contact with blood in the blood stream. The efficacy of the pharmaceutical products is not cancelled out by the formation of insoluble salts.

The sparingly soluble salt again releases the unchanged pharmaceutical substance following its detachment from the medicinal product. This completely satisfies the requirements for the extraordinarily small amounts of pharmaceutical product which are necessary to be effective when administered locally. The same principle can be used for hydrophilic water soluble additives. The change to a sparingly soluble salt creates a sparingly water soluble matrix structure which protects a hydrophilic and/or water soluble active substance from premature detachment for a certain period of time e.g. during the manipulation of a balloon catheter before the actual dilatation of the vessel and before the actual detachment of the substance.

The insoluble salts can be produced before the use of the hydrophilic and/or water soluble substances for coating the medicinal products and can then be used in the form of suspensions in suitable carrier liquids. A preferred method is to coat the medicinal products with the soluble form in an aqueous solution or in an organic solvent which contains water or in a relatively hydrophilic organic solvent or a solvent mixture. The solvent is then evaporated and the surface which has just been coated is next treated with a precipitating agent for use with the hydrophilic and/or water soluble substances so that the subsequent change into the insoluble salt or the insoluble electrically neutral form can take place. The precipitating agent can be applied in any preferred form e.g. by immersion, spraying, brushing or using a volume measuring device.

Examples of physiologically acceptable sparingly soluble salts are calcium, magnesium, zinc and iron (II) or iron (III) compounds on the one hand and on the other hand there are phosphates, sulphates, oxalates or also salts of ionic radio contrast media such as diatrizoates.

The present invention therefore concerns the use of at least one low molecular weight, hydrophilic active substance in the form of a sparingly water soluble salt or as a sparingly soluble water soluble acid or a sparingly soluble base for the treatment and prophylaxis of vascular diseases and also for the achievement of lasting effects from one single treatment with immediate bioavailability.

In a further embodiment of this invention the balloon membrane of the catheter balloon with at least one active substance lying open on the surface which is coated in such a way that at least one active substance is immediately released when the catheter balloon is expanded, where at least one water soluble active substance is present as a salt that is sparingly soluble in water or an acid that is sparingly soluble in water or a base that is sparingly soluble in water or else a complex that is sparingly soluble in water.

A similar embodiment of this invention concerns a balloon membrane of the catheter balloon with at least one active surface lying open on the surface which is coated in such a way that at least one active substance is immediately released when the catheter balloon is expanded, where at least one active substance has been converted into a sparingly water soluble form or particularly a salt that is sparingly soluble in water or a base that is sparingly soluble in water or an acid that is sparingly soluble in water or a complex that is sparingly soluble in water after application to the balloon membrane or the hydrophilic balloon membrane or the hydrophilically coated balloon membrane The loss of hydrophilic and/or water soluble active substances from medicinal products during the manipulation of the device, in particular on the way through the insertion sheath or guide catheter to the location where the treatment is to take place can also be achieved by the subsequent coating with physiologically acceptable substances that are slowly or slightly soluble in water. In so doing these substances can achieve a desired pharmacological effect or else act as additives. These additional coatings can be solids or else they can be liquids as is the case with certain lipids. Examples of additional coatings which are solids are sugar, sugar alcohols, other neutral organic substances, lipophilic amino acids, salts of organic and inorganic acids and bases, contrast media that are usually used in medicine or dyes, anticoagulants such as heparin, platelet aggregation inhibitors such as acetylsalicylic acid or salicylic acid and many others. The effectiveness of this kind of special additional coating in protecting any given coating is to be tested on an individual basis. Additional protective coatings are therefore preferably applied so that the solutions are made using solvents in which protective coating is insoluble. For example, acetylsalicylic acid (as an additional protective coating) is readily soluble in ethyl acetate in which many hydrophilic and/or water soluble active substances are very slightly soluble.

Additional protective coatings should be as thin as possible. An application of $<30 \mu g/mm^2$ surface area is preferred.

Additional protective coatings can on the other hand be applied in a variety of ways where the preferred methods are spraying and a very brief immersion.

In a further preferred embodiment the present invention is therefore concerned with balloon catheters which are coated with at least one hydrophilic active substance or a preparation that contains at least one hydrophilic active substance where a further outer protective layer is applied on top of this coating in the form of a biocompatible material that is slightly or only slowly soluble in water.

Balloon catheters are therefore preferred in which at least one active substance or at least one hydrophilic active substance is coated with or impregnated with a layer that is slightly or only slowly soluble in water. The protective layer can penetrate the layer of active substance. It can for example consist of substances which do not have biological effects, but it can also consist of acetylsalicylic acid or heparin.

EXAMPLES

Example 1

Coating of Hydrophilic and Non-Hydrophilic Balloon Catheters with Paclitaxel Test Nos 102/103 and 128/129

Coating solution: 30 mg paclitaxel/ml in acetone 89%, ethanol 9%, Ultravist®-370 (Schering AG, Berlin) 2%, by immersing it 4 times and allowing it to dry between each immersion:

| Type of catheter | Number of balloon catheters | $\mu g$ paclitaxel/mm$^2$ balloon surface | Standard deviation |
|---|---|---|---|
| standard, 3.5 to 15 mm | 5 | 3.4 | 0.5 |
| hydrophilic, 3.5 to 15 mm | 5 | 2.8 | 0.2 |
| standard, 3.5 to 20 mm | 8 | 5.0 | 0.5 |
| hydrophilic 3.5 to 20 mm | 8 | 5.6 | 0.2 |

Conclusion: balloons with hydrophilic surfaces can be reproducibly coated.

Example 2

Coating with a Micro-Dosing Device: Comparison with Coating by Immersion

In the first series (test nos. 323 and 326-329) each time 3 ready folded balloons were either immersed 4 times in coating solution A and in each case they were thoroughly dried between each immersion, or else the active substance was applied twice using 12.5 µl of the same solution and a Hamilton CR-700 constant rate syringe, or 3 further coating solutions were applied using highly volatile organic solvents.

| Test no (n) | Balloon | Condition of the balloons- | Solvent | Concentration of the active substance | | Active substance on the balloon µg/mm$^2$ mean ± SD |
|---|---|---|---|---|---|---|
| | | | | | Number of coatings by immersions | |
| 323 (3) | 3.0-17 | folded | A. | 30 mg/ml | 4 | 4.1 ± 0.7 |
| | | | | | Number of dosing operations and their volumes | |
| 326 (3) | 3.0-17 | folded | A | 30 mg/ml | 2 × 12.5 µl | 3.6 ± 0.0 |
| 327 (3) | 3.0-17 | folded | B | 30 mg/ml | 2 × 12.5 µl | 3.6 ± 0.1 |
| 328 (3) | 3.0-17 | folded | C | 30 mg/ml | 2 × 12.5 µl | 3.8 ± 0.1 |
| 329 (3) | 3.0-17 | folded | D | 30 mg/ml | 2 × 12.5 µl | 3.7 ± 0.0 |

Applying the dosage using the Hamilton syringe leads to a significantly more accurate dosage on the balloon.

Uniformity of the dosage was also successful on balloons of different sizes (tests 390/391) and was more accurate than when coating by immersion (392).

| Test no (n) | Balloon | Condition of the balloon- | Solvent | Concentration of the active substance | Number of dosing operations and their volumes | Active substance on the balloon µg/mm² mean ± SD |
|---|---|---|---|---|---|---|
| 390 (4) | 3.5-20 | folded | A | 30 mg/ml | 2 × 14 µl | 3.7 ± 0.1 |
| 391 (4) | 2.0-14 | folded | A | 30 mg/ml | 2 × 6 µl | 3.6 + 0.1 |
|  |  |  |  |  | Number of coatings by immersion |  |
| 392 (4) | 3.5-20 | folded | A | 30 mg/ml | 4 | 4.4 ± 0.4 |

The distribution of the active substance along the longitudinal axis of the balloons was investigated for each of 3×100 mm long PTA balloons of 5 mm diameter. The balloons were cut into 10 mm long pieces after coating with either the dosing operation using the Hamilton syringe (see FIG. 1) or by immersion (see FIG. 2). The content of the active substance in the pieces of balloon were measured using HPLC. In the illustration a value of 1 on the y axis corresponds to the average quantity distributed over the entire length i.e. it is a perfectly even distribution.

Figure 1:
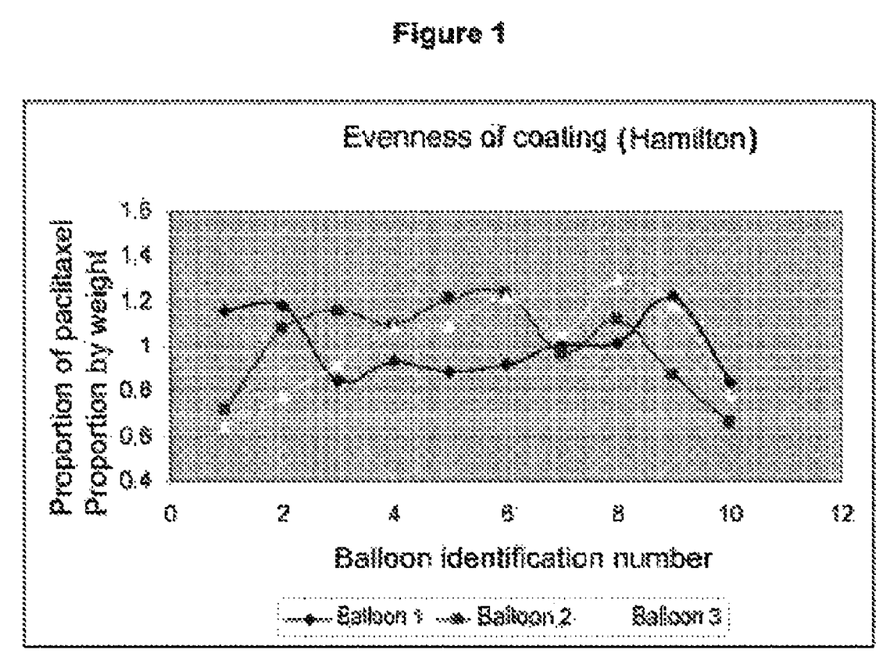
FIG. 1 is a graph showing evenness of coating using the Hamilton method as described in Example 2.
Figure 2:
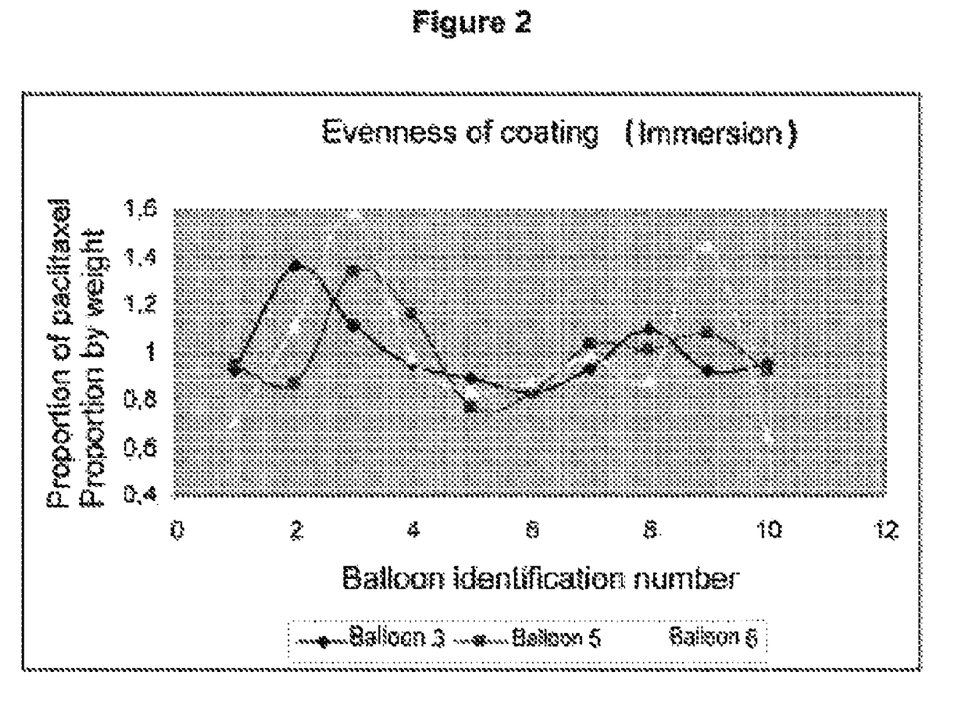
FIG. 2 is a graph showing evenness of coating using the immersion method as described in Example 2.

The distribution of the active substance on the longitudinal axis of the balloon after application using the dosing operation is in no single case more uneven than using immersion, or rather it is in fact more uniform than immersing the balloon (see FIGS. 1 and 2).

Example 3

Device to Apply the Coating Solution for Use on the Balloon:

Preferably using a needle with a narrow lumen which is 2 to 10 cm long with proximally a connection to the microdosing apparatus, the distal end is closed. The needle has an outlet at the side in the form of a curved recess which fits the curvature of the balloon (see FIG. 3).

Example 4

Coating the Balloon Catheters with Methotrexate

Coating Solution:
30 mg methotrexic acid+100 µl sodium bicarbonate (7.5%)+900 µl methanol (coating with 2×16 µl, corresponding to ~4 µg/mm² balloon surface)
Balloons: 3.5 to 19 mm
Additional coat: Ultravist®-370+hydroxyethyl starch (HES) 10% (1:1 by volume)+30 mg methotrexate/ml applied by immersing for a short time
Stents: stainless steel, balloon-expandable 3.5 to 18 mm
Content of active substance: 5.3 µg/mm² balloon surface Example 5

The efficacy and tolerance of coated balloon catheters according to example 5 in overstretched coronary arteries in pigs Method: Scheller B, Speck U, Abramjuk C, Bernhardt U, Böhm M, Nickenig G: Paclitaxel balloon coating—a novel method for prevention and therapy of restenosis. Circulation 2004; 110:810-4

Stents were implanted into pigs with the help of methotrexate coated or uncoated (control) balloon catheters. After 4 weeks the extent of the constriction of the lumen in the area of the stent was measured using quantitative angiography.
Results:

|  | Control n = 9 | Methotrexate n = 8 | p |
|---|---|---|---|
| Reference diameter [mm] | 2.41 ± 0.28 | 2.30 ± 0.39 | 0.495 |
| Stent diameter [mm] | 2.64 ± 0.13 | 2.41 ± 0.29 | 0.045 |
| Rate of overexpansion [—] | 1.11 ± 0.14 | 1.07 ± 0.20 | 0.068 |
| Reference diameter 28d [mm] | 2.35 ± 0.39 | 2.38 ± 0.26 | 0.840 |
| Minimum vessel diameter 28d [mm] | 1.54 ± 0.32 | 1.74 ± 0.41 | 0.273 |
| Late lumen loss [mm] | 1.10 ± 0.33 | 0.67 ± 0.39 | 0.025 |

The late lumen loss means the amount by which the original coronary artery lumen diameter decreases due to excessive cell growth within 4 weeks. With blood flowing through them the original coronary artery lumen diameters were 2.64 mm and 2.41 mm respectively. In the control group (no methotrexate) the late lumen loss was 1.1 mm and in the group treated with methotrexate the late lumen loss was 0.67 mm. Methotrexate has significantly reduced (p<0.025) the unwanted proliferation of the arterial wall which constricted the vascular lumen.

Example 6

Coating of Balloon Catheters with Thalidomide

Falcon Bravo RX 3.5 to 20 mm, Invatec S.R.L., Roncadelle, Italy 8 items;
Coating solution:
Dimethylformamide+50 mg/ml thalidomide
Coat each balloon 2 times with 8 µl and leave to dry for at least 12 hours after each coating.
Afterwards immerse 4 balloons for a short time in 50 mg trimyristine in 3 ml warm ethyl acetate.
Loss by means of the insertion sheath, the guide catheter and by 1 minute in a coronary artery of a pig (not expanded) and then withdrawn. Analysis using HPLC, columns: Waters Symmetry, C18, 5 µm, 25 cm×4.6 mm, mobile phase: 72% by volume 0.01M ammonium acetate buffer pH 5.5 and 28% by volume acetonitrile, 0.8 ml/min; detection: at 300 nm.
The balloons treated with trimyristate lost an average of 28% of the active substance on the way to the coronary arteries and back, the balloons which were not treated with trimyristate lost 95% i.e. the trimyristate coating had significantly improved the adhesion of the thalidomide to the balloon.

Example 7

Coating of Balloon Catheters with Arsenic Trioxide

Falcon Bravo RX 3.5 to 20 mm, Invatec S.R.L., Rocadelle, Italy 12 items
Coating solution:
50 mg $As_2O_3$ are dissolved in 1 ml water for injection; the solution is diluted with 3 ml acetone or methanol.
Coat each balloon 3 times with 25 µl and leave to dry for at least 12 hours after each coating.
Loss by means of the insertion sheath, the guide catheter and by 1 minute in a coronary artery of a pig (not expanded) and then withdrawn, or following expansion in a coronary artery for 1 minute; analysis by atomic absorption spectrometry after ashing.
The balloons lost on average 25% of the active substance on the way to the coronary arteries and back. After expansion in the arteries on average 13% of the dose remained on the balloons (in each case n=4).

Example 8a

Control of Adhesion Using Just the Solvent (Series 1)

Falcon Bravo RX 3.5 to 20 mm, Invatec S.R.L., Rocadelle, Italy 12 items
Each balloon was coated in the folded state with 3 to 4 µg/mm² paclitaxel and was tested for loss of the active substance during expansion in the dry state as defined under 'Definitions'.

| | |
|---|---|
| Acetone | 21% |
| Dioxane | 12% |
| Dimethylformamide | 24% |
| Dimethylsulfoxide | 66% |
| Acetic acid | 4% |
| Isopropanol | 19% |
| Tetrahydrofuran | 4% |

Example 8b

Control of Adhesion Using Just the Addition of Water Up to the Limit of Solubility for Water in Tetrahydrofuran (THF) at Room Temperature (Series 2)

| | |
|---|---|
| Tetrahydrofuran | 3% |
| Tetrahydrofuran with 10% water by volume | 3% |
| Tetrahydrofuran with 20% water by volume | 16% |
| Tetrahydrofuran with 37% water by volume | 37% |

Example 9

Coating a Balloon Catheter with the Addition of Urea

Falcon Bravo RX 3.5 to 20 mm, Invatec S.R.L., Roncadelle, Italy 8 items;

Coating solution:
70 mg urea dissolved in 1 ml water+9 ml tetrahydrofuran+500 mg paclitaxel Coating each balloon once with 18 µl.

The invention claimed is:

1. A balloon catheter including a catheter balloon comprising a balloon membrane coated with at least one active substance and at least one additive lying on the surface of said catheter balloon membrane, the balloon membrane coated in such a way that the at least one active substance is immediately released when the catheter balloon is expanded, wherein the additive comprises ascorbic acid.

2. The balloon catheter according to claim 1, wherein the at least one active substance is a sparingly water soluble active substance.

3. The balloon catheter according to claim 2, wherein the sparingly water soluble active substance is a sparingly water soluble salt or a sparingly water soluble acid or a sparingly water soluble base or a sparingly water soluble complex.

4. The balloon catheter according to claim 1, wherein the catheter balloon is prepared using a coating mixture comprising at least one hydrophilic solvent optionally mixed with water.

5. The balloon catheter according to claim 4, wherein the hydrophilic solvent is an organic solvent and contains methanol, ethanol, (iso-) propanol, acetone, tetrahydrofuran, acetic acid, dioxane or dimethylformamide.

6. The balloon catheter according to claim 1, wherein the catheter balloon comprises a smooth-walled balloon membrane.

7. The balloon catheter according to claim 6, wherein the catheter balloon provided with said smooth-walled balloon membrane is coated in a folded state.

8. The balloon catheter according to claim 1, wherein the balloon membrane is coated with less than 1 µg/mm2 of non-volatile components.

9. The balloon catheter according to claim 8, wherein the balloon membrane is coated with less than 5 µg/mm2 of non-volatile components.

10. The balloon catheter according to claim 1, wherein the balloon membrane of the catheter balloon is treated with activated oxygen.

11. The balloon catheter according to claim 1, wherein the catheter balloon is additionally coated with other additives.

12. The balloon catheter according to claim 1, wherein the radius of the catheter balloon is increased by more than 15% following complete unfolding of the catheter balloon by means of a pressure increase applied inside the catheter balloon.

13. The balloon catheter according to claim 1, wherein the catheter balloon has a bursting pressure of below 10,000 hPa.

14. The balloon catheter according to claim 1, wherein the catheter balloon has a diameter that is at least 20% greater than a reference diameter of a target artery.

15. The balloon catheter according claim 1, wherein the balloon membrane is a hydrophilic balloon membrane or hydrophilically coated balloon membrane.

16. The balloon catheter according to claim 1, wherein the at least one active substance is coated with or impregnated with a slightly or slowly water soluble biocompatible layer.

17. The balloon catheter according to claim 1, wherein the catheter balloon contains additional protective coatings.

18. The balloon catheter according to claim 1, prepared by coating the surface with a coating preparation comprising the at least one active substance and at least one highly volatile solvent or at least one chlorinated or fluorinated compound with a boiling point below 300° C.

19. The balloon catheter according to claim 1, wherein the catheter balloon is coated with a gel wherein the at least one active substance functions as a gelling agent itself or takes part in gel formation.

20. The balloon catheter according to claim 1, prepared by coating the surface with an active substance dissolved in an organic solvent which contains at least 1% water, and subsequently drying and sterilizing, wherein the active substance is present on the balloon membrane in a crystalline form.

21. The balloon catheter according to claim 1, wherein the balloon membrane of the catheter balloon is smooth walled and is coated with paclitaxel crystals lying on the surface in such a way that at least 70% of the paclitaxel continues to adhere to the surface when a folded balloon is introduced into an artery, the at least 70% of the paclitaxel being immediately released when the catheter balloon is expanded in a constricted artery.

22. The balloon catheter according to claim 1, wherein the at least one active substance comprises methotrexic acid, arsenic or arsenic compounds, bismuth or bismuth compounds, or thalidomide.

23. The balloon catheter according to claim 1, the balloon catheter being suitable for the localised treatment and prophylaxis of vascular diseases.

24. The balloon catheter according to claim 1, the balloon catheter being suitable for the treatment of changes to the vascular wall which do not significantly restrict the flow of blood.

25. The balloon catheter according to claim 1, wherein the catheter balloon has a bursting pressure of below 5000 hPa.

26. The balloon catheter according to claim 1, wherein the catheter balloon comprises a smooth-walled balloon membrane and is prepared by coating the smooth-walled balloon membrane with an active substance dissolved in an organic solvent which contains at least 10% water, and subsequently drying and sterilizing, wherein the active substance is present on the balloon membrane in a crystalline form.

27. The balloon catheter according to claim 1, wherein the balloon membrane of the catheter balloon is smooth walled and is coated with paclitaxel crystals lying on the surface in such a way that at least 80% of the paclitaxel continues to adhere to the balloon surface when the folded balloon is introduced into an artery and is immediately released when the catheter balloon is expanded in a constricted artery.

28. The balloon catheter according to claim 1, wherein the at least one active substance comprises paclitaxel.

29. The balloon catheter according to claim 1, wherein the radius of the catheter balloon is increased by more than 30% following complete unfolding by means of a pressure increase applied inside the catheter balloon.

30. A balloon catheter comprising a balloon surface with at least one active substance and at least one additive that lie on the surface, the substance being immediately released when the catheter balloon is expanded, and wherein the radius of the catheter balloon is increased by more than 15% following complete unfolding of the catheter balloon by means of a pressure increase applied inside the catheter balloon, wherein the additive comprises ascorbic acid.

31. The balloon catheter according to claim 30, wherein the radius of the catheter balloon is increased by more than 30% following the complete unfolding by means of a pressure increase applied inside the catheter balloon.

32. The balloon catheter according to claim 30, wherein the at least one active substance comprises paclitaxel.

* * * * *